United States Patent
Roeder et al.

(10) Patent No.: US 10,660,770 B2
(45) Date of Patent: May 26, 2020

(54) METHOD OF MAKING AN INTERNAL BIDIRECTIONAL BRANCH

(71) Applicant: Cook Medical Technologies LLC, Bloomington, IN (US)

(72) Inventors: Blayne A. Roeder, Bloomington, IN (US); Chantelle King, Brisbane (AU); Nuno Dias, Malmo (SE); Marcelo Ferreira, Rio de Janeiro (BR)

(73) Assignee: Cook Medical Technologies LLC, Bloomington, IN (US)

( * ) Notice: Subject to any disclaimer, the term of this patent is extended or adjusted under 35 U.S.C. 154(b) by 365 days.

(21) Appl. No.: 15/652,561

(22) Filed: Jul. 18, 2017

(65) Prior Publication Data

US 2019/0021887 A1   Jan. 24, 2019

(51) Int. Cl.
*A61F 2/852* (2013.01)
*A61F 2/07* (2013.01)
*A61F 2/06* (2013.01)

(52) U.S. Cl.
CPC ............ *A61F 2/852* (2013.01); *A61F 2/07* (2013.01); *A61F 2002/061* (2013.01); *A61F 2002/075* (2013.01); *A61F 2220/0075* (2013.01); *A61F 2240/001* (2013.01)

(58) Field of Classification Search
CPC ...... A61F 2/852; A61F 2/07; A61F 2002/075; A61F 2240/001; A61F 2002/061; A61F 2220/0075
USPC .......... 600/36, 37; 623/1.11–1.15, 1.22, 1.35
See application file for complete search history.

(56) References Cited

U.S. PATENT DOCUMENTS

| | | | |
|---|---|---|---|
| 6,030,414 A | 2/2000 | Taheri | |
| 6,036,723 A * | 3/2000 | Anidjar | A61F 2/07 623/1.13 |
| 6,238,430 B1 * | 5/2001 | Klumb | A61F 2/88 606/108 |
| 7,722,663 B1 * | 5/2010 | Austin | A61F 2/07 623/1.22 |
| 8,021,419 B2 | 9/2011 | Hartley et al. | |

(Continued)

FOREIGN PATENT DOCUMENTS

| AU | 2016210717 B1 | 5/2017 |
|---|---|---|
| EP | 2749249 A2 | 7/2014 |

(Continued)

OTHER PUBLICATIONS

Partial European Search Report for corresponding EP Application No. 18275097 dated Mar. 8, 2019, 6 pages.

*Primary Examiner* — Navin Natnithithadha
*Assistant Examiner* — Sunita Reddy
(74) *Attorney, Agent, or Firm* — Brinks Gilson & Lione (57) ABSTRACT

A method of making an internal bidirectional branch and an endoluminal prosthesis from a tubular segment of graft material. The tubular segment is partitioned into first and second sections along a length of the tubular segment. The first section has a width less than a width of the tubular segment, and the second section has a width less than the first section. The second section is partitioned into at least three sub-sections. The tubular segment is connected along a lateral edge of the first and third sub-sections of the second section. The tubular segment is turned inside out such that the bidirectional branch is positioned within a lumen of the first section and an opening of the second sub-section is exposed.

20 Claims, 6 Drawing Sheets

(56) References Cited

U.S. PATENT DOCUMENTS

| | | |
|---|---|---|
| 8,043,366 B2 | 10/2011 | Brown et al. |
| 8,187,313 B2 | 5/2012 | Grabowski et al. |
| 8,337,546 B2 | 12/2012 | Bruszewski |
| 8,545,549 B2 | 10/2013 | Hartley et al. |
| 8,747,455 B2 | 6/2014 | Greenberg |
| 8,915,955 B2 | 12/2014 | West et al. |
| 9,101,457 B2 | 8/2015 | Benary |
| 2002/0156521 A1* | 10/2002 | Ryan .................. A61F 2/07 623/1.13 |
| 2004/0230289 A1* | 11/2004 | DiMatteo ............ A61F 2/07 623/1.13 |
| 2005/0059923 A1 | 3/2005 | Gamboa |
| 2006/0095118 A1* | 5/2006 | Hartley .............. A61F 2/07 623/1.35 |
| 2007/0265697 A1* | 11/2007 | Goicoechea ......... A61F 2/82 623/1.15 |
| 2008/0109066 A1 | 5/2008 | Quinn |
| 2008/0139915 A1* | 6/2008 | Dolan ................. A61B 5/06 600/407 |
| 2009/0259290 A1* | 10/2009 | Bruszewski .......... A61F 2/07 623/1.13 |
| 2009/0259298 A1* | 10/2009 | Mayberry ............ A61F 2/07 623/1.35 |
| 2010/0137973 A1 | 6/2010 | Sutermeister et al. |
| 2010/0179636 A1* | 7/2010 | Mayberry ............ A61F 2/954 623/1.11 |
| 2010/0324664 A1 | 12/2010 | Holzer et al. |
| 2011/0054586 A1* | 3/2011 | Mayberry ............ A61F 2/07 623/1.11 |
| 2011/0093002 A1 | 4/2011 | Rucker et al. |
| 2013/0041456 A1* | 2/2013 | Greenberg ........... A61F 2/07 623/1.35 |
| 2013/0079870 A1* | 3/2013 | Roeder ................ A61F 2/07 623/1.35 |
| 2013/0116775 A1* | 5/2013 | Roeder ................ A61F 2/856 623/1.35 |
| 2014/0277347 A1* | 9/2014 | Daugherty ........... A61F 2/856 623/1.11 |
| 2014/0277348 A1 | 9/2014 | Roeder |
| 2014/0324150 A1* | 10/2014 | Stephens ............. A61F 2/954 623/1.11 |
| 2015/0119975 A1* | 4/2015 | Mastracci ............ A61F 2/856 623/1.35 |
| 2016/0184115 A1* | 6/2016 | Ondersma ........... A61F 2/856 623/1.35 |

FOREIGN PATENT DOCUMENTS

| | | |
|---|---|---|
| WO | WO 2006/028925 | 3/2006 |
| WO | WO 2006/034276 A1 | 3/2006 |

* cited by examiner

METHOD OF MAKING AN INTERNAL BIDIRECTIONAL BRANCH

BACKGROUND

1. Technical Field

The present invention relates to methods of making an internal bidirectional branch within an endoluminal prosthesis, such as for branched endovascular procedures.

2. Background Information

Endovascular aortic aneurysm repair is practiced by a wide range of physicians across varying specialties. An aortic aneurysm is an enlargement of the aorta of a patient caused by weakening in the wall of the aorta. If an aortic aneurysm is untreated, it may rupture and cause serious health complications.

The surgical procedure for endovascular aortic aneurysm repair involves the placement of a stent graft within the aorta of a patient to seal off the aneurysm from blood flow to prevent the aneurysm from expanding. Physicians often use the procedure to treat abdominal aortic aneurysms (AAA), thoracic aortic aneurysms (TAA), thoraco-abdominal aortic aneurysms (TAAA), and aneurysms in other locations of the patient.

The aorta has many branches to other vessels or arteries, such as the renal arteries, the superior mesenteric artery (SMA), the inferior mesenteric artery, and the left and right internal iliac arteries. Branch vessels are also connected to the head, arms, spinal cord, intestines and/or kidneys. Endovascular repair of aneurysms occurring at or near branch vessels requires that blood flow to the branch vessel is maintained and access to the branch vessel for cannulation is available.

Stent grafts may include internal branches to cannulate branch vessels and to maintain blood flow to the branch vessels. However, these internal branches often only include a small opening or access in one direction within the stent graft for physicians to cannulate the branch vessel. Often times, it is unknown or not clear which direction the branch vessel is best cannulated. These factors increase the difficulty of cannulation, which can lead to complications during the surgical procedure for endovascular aortic aneurysm repair.

BRIEF SUMMARY

This invention concerns a method of making an internal bidirectional branch within an endoluminal prosthesis that enables cannulation of a branch vessel from several directions and allows surgeons the ability to access the outside of the endoluminal prosthesis through the bidirectional branch from several directions. The method also provides a simplified construction of an endoluminal prosthesis with a bidirectional branch and eliminates the need for making a separate branch for connection to an endoluminal prosthesis.

The present invention relates to a method of making a bidirectional branch within an endoluminal prosthesis. The method includes laying a tubular segment of graft material flat. The tubular segment of graft material includes a first lateral edge, a second lateral edge, a width extending from the first lateral edge to the second lateral edge, and a length extending from a proximal end to a distal end of the tubular segment. The method also includes partitioning the tubular segment into first and second sections along the length of the tubular segment. The first section extends from the first lateral edge toward the second lateral edge and includes a width less than the width of the tubular segment. The second section extends from the second lateral edge toward the first lateral edge and includes a width less than the width of the first section such that a total width of the first and second sections is the same as the width of the tubular segment. The method also includes partitioning the second section of the tubular segment into at least three sub-sections. A first sub-section extends from the proximal end toward the distal end for a length, a second sub-section extends from the first sub-section toward the distal end for a length, and a third sub-section extends from the second sub-section to the distal end and has a length. A total length of the three sub-sections is the same as the length of the tubular segment. The method further includes connecting the tubular segment along a lateral edge of the first sub-section from the proximal end to the second sub-section and along a lateral edge of the third sub-section from the distal end to the second sub-section. The lateral edges of the first and third sub-sections are opposite the second lateral edge of the tubular segment. The method also includes turning the tubular segment inside out such that the first, second and third sub-sections of the second sub-section form the bidirectional branch, the bidirectional branch is positioned within a lumen of the endoluminal prosthesis, and an opening of the third sub-section is exposed.

A method of making an internal bidirectional branch for an endoluminal prosthesis from a tubular segment of graft material. The method includes partitioning a tubular segment of graft material into two tubular sections. The tubular segment of graft material having a lumen, a diameter, and a length extending from a proximal end to a distal end of the tubular segment. Each tubular section having the same length as the tubular segment of graft material. The first tubular section includes a diameter less than the diameter of the tubular segment of graft material, and the second tubular section includes a diameter less than the diameter of the first tubular section such that a total diameter of the first and second tubular sections is the same as the diameter of the tubular segment of graft material. The method also includes partitioning the second tubular section into five sub-sections along the length of the tubular segment of graft material, wherein a total length of the five sub-sections is the same as the length of the tubular segment of graft material. A first sub-section extends from the proximal end toward the distal end for a length, a second sub-section extends from the first section toward the distal end for a length, a third sub-section extends from the second sub-section toward the distal end for a length, a fourth sub-section extends from the third sub-section toward the distal end for a length, and a fifth sub-section extends from the fourth section to the distal end and has a length. The method also includes connecting the tubular segment of graft material along the first, second, fourth, and fifth sub-sections of the second tubular section to separate the first tubular section and the second tubular section and removing the first and fifth sub-sections of the second tubular section from the tubular segment while maintaining connected edges of the first and fifth sub-sections such that the second, third and fourth sub-sections form the bidirectional branch. The method further includes turning the tubular segment inside out such that the bidirectional branch is positioned within a main lumen of the endoluminal prosthesis and an opening of the third sub-section is exposed.

A method of making an internal bidirectional branch for an endoluminal prosthesis including laying a tubular segment of graft material flat. The tubular segment of graft material includes a first lateral edge, a second lateral edge, a width extending from the first lateral edge to the second lateral edge, and a length extending from a proximal end to a distal end of the tubular segment. The method also includes partitioning the tubular segment into first and second sections along the length of the tubular segment. The first section extends from the first lateral edge toward the second lateral edge and has a width less than the width of the tubular segment, and the second section extends from the second lateral edge toward the first lateral edge and has a width less than the width of the first section such that a total width of the first and second sections is the same as the width of the tubular segment. The method also includes partitioning the second section of the tubular segment into at least three sub-sections, wherein each section has the width of the second section. A first sub-section extends from the proximal end toward the distal end for a length, a second sub-section extends from the first sub-section toward the distal end for a length, and a third sub-section extends from the second section to the distal end and has a length. A total length of the five sections is the same as the length of the tubular segment. The method further includes connecting the tubular segment along a lateral edge of the first sub-section from the proximal end to the second sub-section and along a lateral edge of the third sub-section from the distal end to the second sub-section. The lateral edges of the first and third sub-sections are opposite the second lateral edge of the tubular segment. The method also includes turning the tubular segment inside out such that the first, second and third sub-sections of the second section form the bidirectional branch, the bidirectional branch is positioned within a lumen of the endoluminal prosthesis, and an opening of the third section is exposed. The method also includes connecting a plurality of stents to an exterior surface of the endoluminal prosthesis.

DETAILED DESCRIPTION OF THE DRAWINGS AND THE PRESENTLY PREFERRED EMBODIMENTS

In the present disclosure, the term "proximal" refers to a direction that is generally closest to the heart during a medical procedure, while the term "distal" refers to a direction that is farthest from the heart during a medical procedure.

The term "prosthesis" refers to any device for insertion or implantation into or replacement for a body part or a function of that body part. The term also may refer to a device that enhances or adds functionality to a physiological system. The term prosthesis may include, for example and without limitation, a stent, stent-graft, filter, valve, balloon, embolization coil, and the like.

Figure 1:
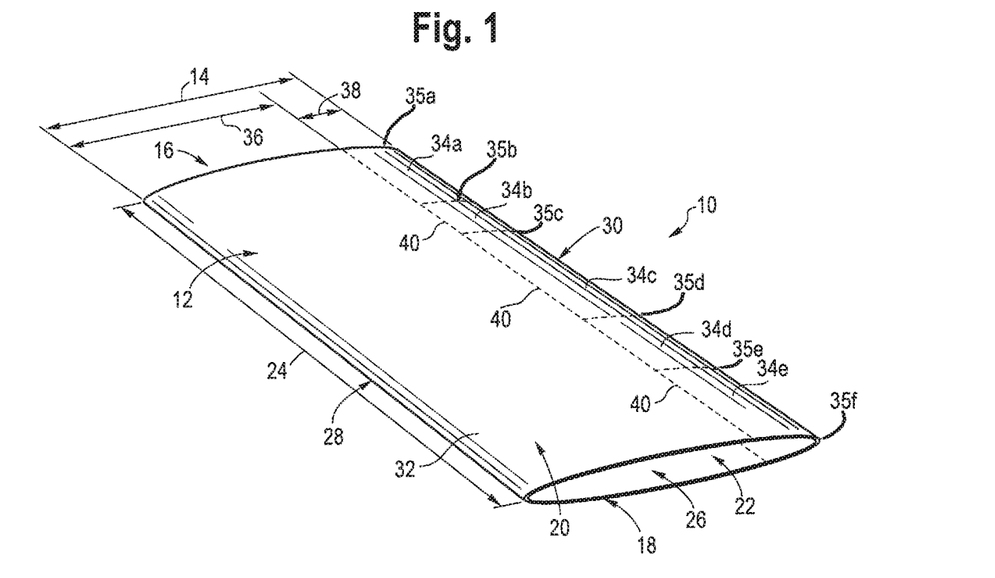
FIG. 1 shows a flattened perspective view of a tubular segment of graft material.

FIG. 1 shows a tubular segment 10 of graft material. The tubular segment 10 includes a tubular body 12, a proximal end 16, a distal end 18, a first surface 20, a second surface 22, a length 24 that extends from the proximal end 16 to the distal end 18, and a lumen 26. The tubular segment 10, as shown in FIG. 1, has been flattened. In the flattened state, the tubular segment 10 also includes a width 14, a first or left lateral edge 28 and a second or right lateral edge 30. In a non-flattened state, the tubular segment 10 has a diameter. The graft material of the tubular segment 10 may include a flexible material, such as polytetrafluoroethylene (PTFE) or expanded PTFE (ePTFE), polyethylene terephthalate (PET), a polyester material, or other stent graft materials known in the art.

Figure 2:
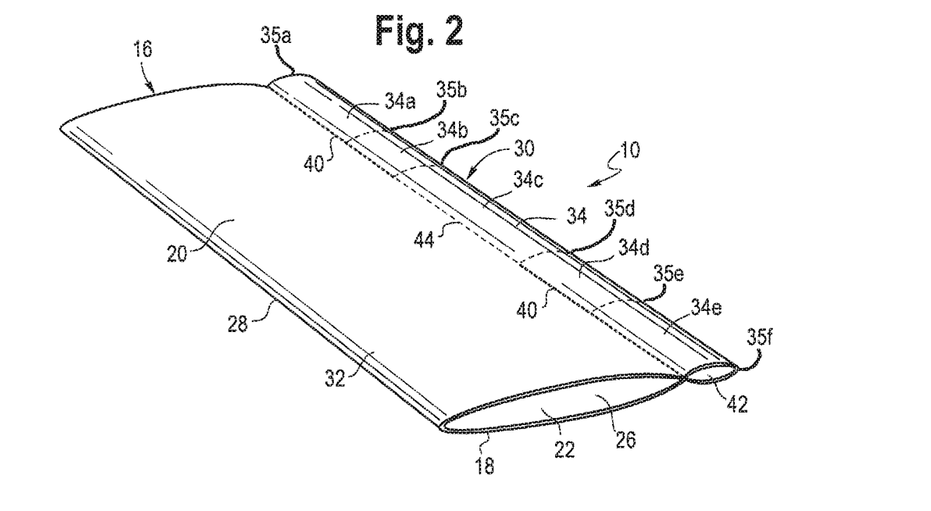
FIG. 2 shows a flattened perspective view of the tubular segment of graft material of FIG. 1 separated into first and second tubular sections.

To form an endoluminal prosthesis with an internal bidirectional branch 48, the tubular segment 10 of graft material is separated into two tubular sections 32, 34 along a partition line 40. Each of the first and second tubular sections 32, 34 has the same length 24 as the tubular segment 10. The first tubular section 32 has a width 36 in the flattened state and a diameter in the non-flattened state. The width 36 and diameter of the first tubular section 32 is less than the width 14 and diameter of the tubular segment 10. The width 36 of the first tubular section 32 extends from the left lateral edge 28 toward the right lateral edge 30 of the tubular segment 10. The second tubular section 34 has a width 38 in the flattened state and a diameter in the non-flattened state. The width 38 and diameter of the second tubular section 34 is less than the width 36 and diameter of the first tubular section 32. The width 38 of the second tubular section 34 extends from the right lateral edge 30 toward the left lateral edge 28, or, in other words, from the first tubular section 32 to the right lateral edge 30. The combined or total width of the first and second tubular sections 32, 34 is the same as the width 14 of the tubular segment 10.

The first or left lateral edge of the first tubular section 32 is the same as the left lateral edge 28 of the tubular segment 10, and the second or right lateral edge of the first tubular section 32 is the partition line 40. The first or left lateral edge of the second tubular section 34 is the partition line 40, and the second or right lateral edge of the second tubular section 34 is the same as the right lateral edge 30 of the tubular segment 10.

Figure 3:
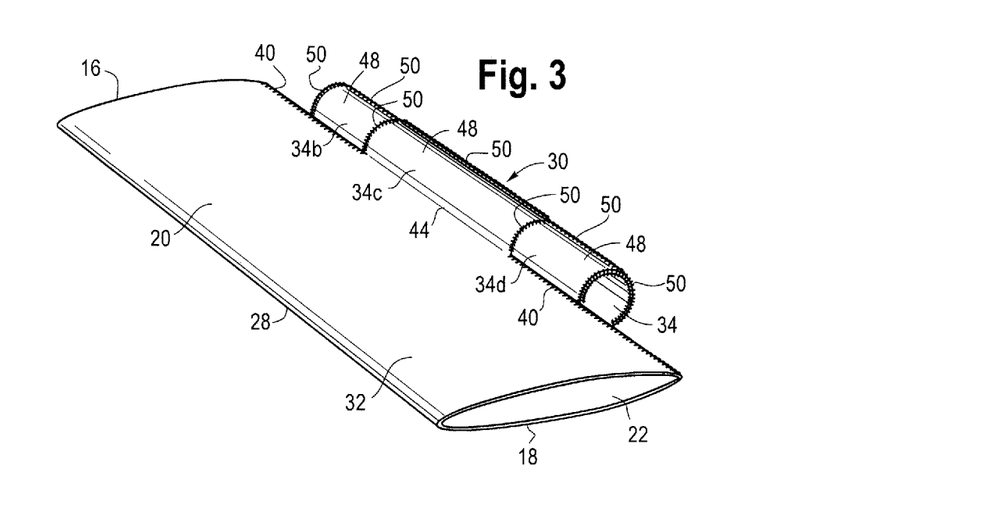
FIG. 3 shows a flatten perspective view of the tubular segment of graft material of FIG. 1 with two sub-sections of the second tubular section removed to form a bidirectional branch.

To form the internal bidirectional branch 48, the second tubular section 34 is separated into five sections or sub-sections 34a, 34b, 34c, 34d, and 34e, as shown in FIG. 1. Each sub-section 34a, 34b, 34c, 34d, and 34e has the same width 38 as the second tubular section 34. Each of the sub-sections has a proximal end and a distal end. 35a-35f with the distal end of each section coincident with an adjacent distal end. The first sub-section 34a extends from the proximal end 16 of the second tubular section and extends toward the distal end 18 for a length from the first sub-section proximal end 35a to the first sub-subsection distal end 35b, the second sub-section 34b extends from the distal end 35b of the first sub-section 34a toward the distal end 18 for a length from the distal end 35b to the distal end 35c of the second sub-section 34b, the third sub-section 34c extends from the distal end 35c of the second sub-section 34b toward the distal end 18 for a length from distal end 35c of the second sub-section to the distal end 35d of the third sub-section, the fourth sub-section 34d extends from the distal 35d end of the third sub-section 34c toward the distal end 18 for a length from the distal end 35d to the distal end of the fourth sub-section, and the fifth sub-section 34e extends from the distal end 35e of the fourth sub-section 34d to the distal end 18 of the second tubular section and comprises a length from the distal end 35e to the distal end 35f of the fifth sub-section. As shown in FIGS. 1-3, the length of the third sub-section 34c may be greater than the lengths of the first, second, fourth and fifth sub-sections 34a, 34b, 34d, 34e, which are approximately equal. In other examples, the lengths of each sub-section 34a, 34b, 34c, 34d, and 34e may be the same or may vary, e.g., depending on a desired axial length of the bidirectional branch 48 relative to the overall axial length of the endoluminal prosthesis, or other considerations.

To separate the first and second tubular sections 32, 34, the tubular segment 10 is connected along the partition line 40 within the first, second, fourth and fifth sub-sections 34a, 34b, 34d, 34e of the second tubular section 34. The tubular segment 10 is connected via sewing or stitching the tubular segment 10 along the partition line 40, as shown in FIG. 2. The tubular segment 10 remains unconnected along the partition line 40 within the third sub-section 34c to create an opening 44 for the second tubular section 34 that is described in further detail below. The separation of the first and second tubular sections 32, 34 creates a lumen 42 of the second tubular section 34.

The second, third, and fourth sub-sections 34b, 34c, 34d form the internal bidirectional branch 48 and therefore the first and fifth sub-sections 34a, 34e are removed. The first and fifth sub-sections 34a, 34e of the second tubular section 34 are removed from the tubular segment 10 by cutting adjacent to the partition line within the first and fifth sub-sections 34a, 34e and along respective ends of the first and fifth sub-sections 34a, 34e adjacent to the second sub-section 34b and the fourth sub-section 34d, respectively. As shown in FIG. 3, during the cutting and removal of the first and fifth sub-sections 34a, 34e, the sewn partition line 40 within the first and fifth sub-sections 34a, 34e is maintained such that the first tubular section 32 is not open or otherwise exposed along the partition line 40 where the first and fifth sub-sections 34a, 34e previously were connected.

In an alternative embodiment (not shown), to form the internal bidirectional branch, the second tubular section 34 is separated into three sections or sub-sections rather than five sections or sub-sections such that the first sub-section comprises sub-sections 34a and 34b of the previously described embodiment, the second sub-section comprises sub-section 34c of the previously described embodiment, and the third sub-section comprises sub-sections 34d and 34e of the previously described embodiment. In addition to comprising three sub-sections rather than five sub-sections, the first and third sub-sections of the alternative embodiment may not be cut and removed. In this alternative embodiment, the internal bidirectional branch would comprise a length that is equal to the length 24 of the tubular segment 10. The method of making the alternative embodiment of bidirectional branch would otherwise include the same steps described above and below regarding the endoluminal prosthesis comprising the internal bidirectional branch 48.

To support the patency and shape of the internal bidirectional branch 48, wire 50 is added to the internal bidirectional branch 48, as shown in FIG. 3. Wire 50 may include nitinol wire or a bow wire and is added via stitching or sewing wire 50 to the graft material of the tubular segment 10. Wire 50 is added to the internal bidirectional branch 48 around proximal and distal ends of the second and fourth sub-sections 34b, 34d, as shown in FIG. 3, and along the right lateral edge 30 within the second and fourth sub-sections 34b, 34d. Wire is also added along the right lateral edge 30 within the third sub-section 34c. In one example, nitinol wire is added to the internal bidirectional branch 48 around proximal and distal ends of the second and fourth sub-sections 34b, 34d and along the right lateral edge 30 within the second and fourth sub-sections 34b, 34d, and a bow wire is added along the right lateral edge 30 within the third sub-section 34c. In other examples, wire 50 may be added at additional locations or areas on the second and fourth sub-sections 34b, 34d to support the shape of the internal bidirectional branch 48.

Figure 4:
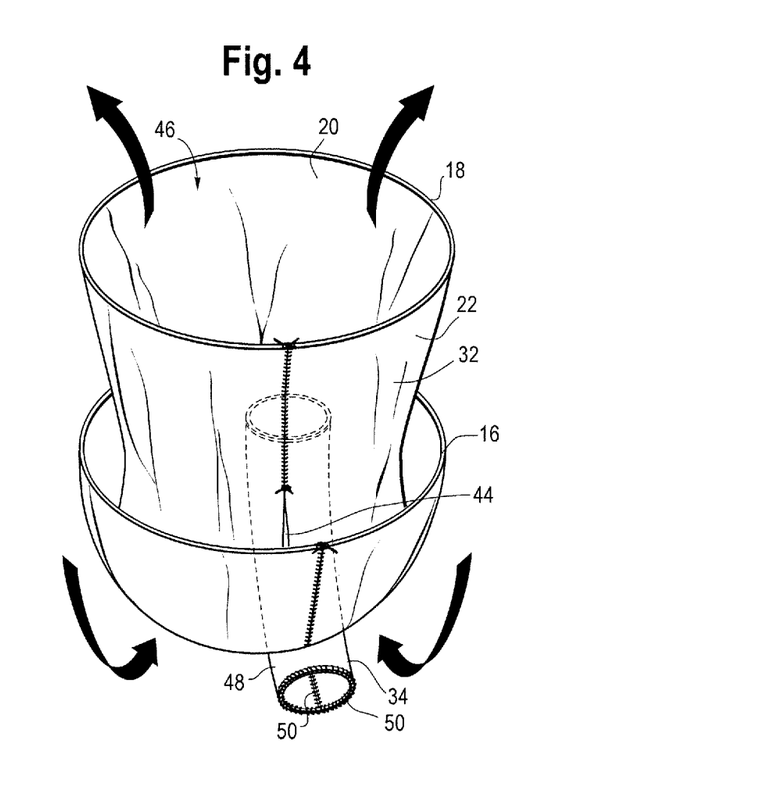
FIG. 4 shows a perspective view of turning the tubular segment of graft material of FIG. 1 inside out.

After removal of the first and fifth sub-sections 34a, 34e and the addition of wire 50 to the internal bidirectional branch 48, the tubular segment 10 is turned inside out to form an endoluminal prosthesis 54, as shown in FIG. 4, such that the internal bidirectional branch 48 is located inside or internally within a main lumen 46 of the endoluminal prosthesis 54. Prior to turning the tubular segment 10 inside out, the first surface 20 of the first tubular section 32 was located on the exterior of the tubular segment 10 and the second surface 22 of the first tubular section 32 was located on the interior of the tubular segment 10, as shown in FIGS. 1-3. After the tubular segment 10 is turned inside out, the second surface 22 of the first tubular section 32 forms the exterior of the endoluminal prosthesis 54 and the first surface 20 of the first tubular section 32 forms the interior of the endoluminal prosthesis 54.

Figure 5:
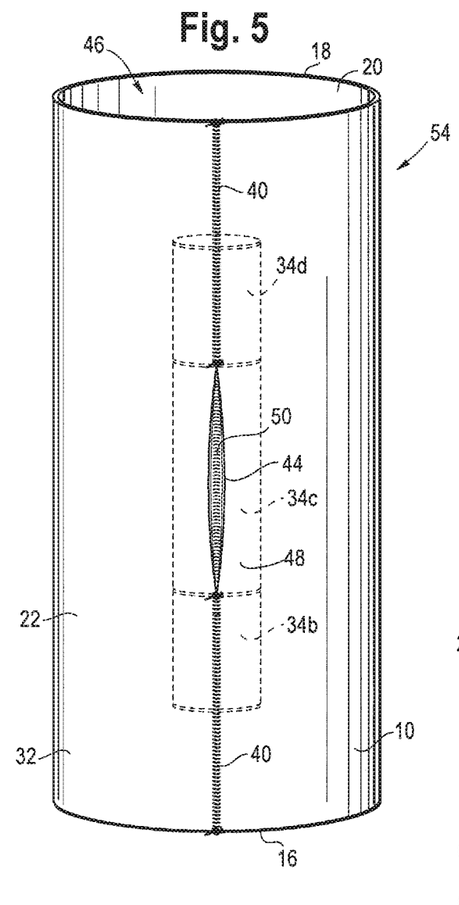
FIG. 5 shows a side view of the tubular segment of graft material of FIG. 1 after being turned inside out.

FIG. 5 shows a side view of the endoluminal prosthesis 54 with the internal bidirectional branch 48 located internally within the main lumen 46 of the endoluminal prosthesis 54. After turning the tubular segment 10 inside out, the opening 44 of the internal bidirectional branch 48 is exposed. As shown in FIG. 5, the opening 44 forms an oval-shaped slit prior to expansion, which is described in detail below.

A plurality of stents 52 may be added to the exterior of the endoluminal prosthesis 54, which is the second surface 22 of the first tubular section 32, to support the shape of the endoluminal prosthesis 54 and to facilitate positioning of the endoluminal prosthesis 54 within the aorta. The plurality of stents 52 may include Z-stents, Gianturco stent design or other stent designs. In one example, as shown in FIG. 6, the plurality of stents 52 connected to the endoluminal prosthesis 54 are Z-stents.

Each Z-stent may include a series of substantially straight segments or struts interconnected by a series of bent segments or bends. The bent segments may include acute bends or apices. The Z-stents are arranged in a ZigZag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, external stents may have the potential to become intertwined with the wires or other devices utilized to ensure branch vessel access, sealing, and fixation. Thus, in some instances, it may be desirable to affix some of the stents 52 to the interior or first surface 20 of the first tubular section 32 and/or to exterior and interior surfaces of the internal bidirectional branch 48.

Figure 6:
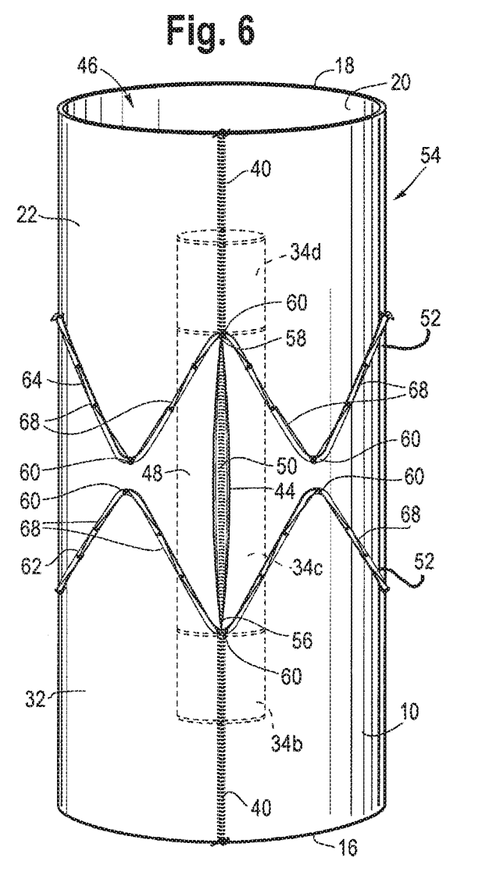
FIG. 6 shows a side view of the tubular segment of graft material of FIG. 1 after being turned inside out with a plurality of stents.

The plurality of stents 52 include at least two rows 62, 64 of stents, as shown in FIG. 6. The plurality of stents 52 are positioned around the opening 44 of the internal bidirectional branch 48 such that an apex 60 of the first row 62 of Z-stents align with a proximal end 56 of the opening 44 and an apex 60 of the second row 64 of Z-stents align with a distal end 58 of the opening 44, as shown in FIG. 6. In this configuration, the Z-stents form a quadrilateral around the opening 44. The quadrilateral may include the shape of a parallelogram and/or a rhombus.

Figure 7:
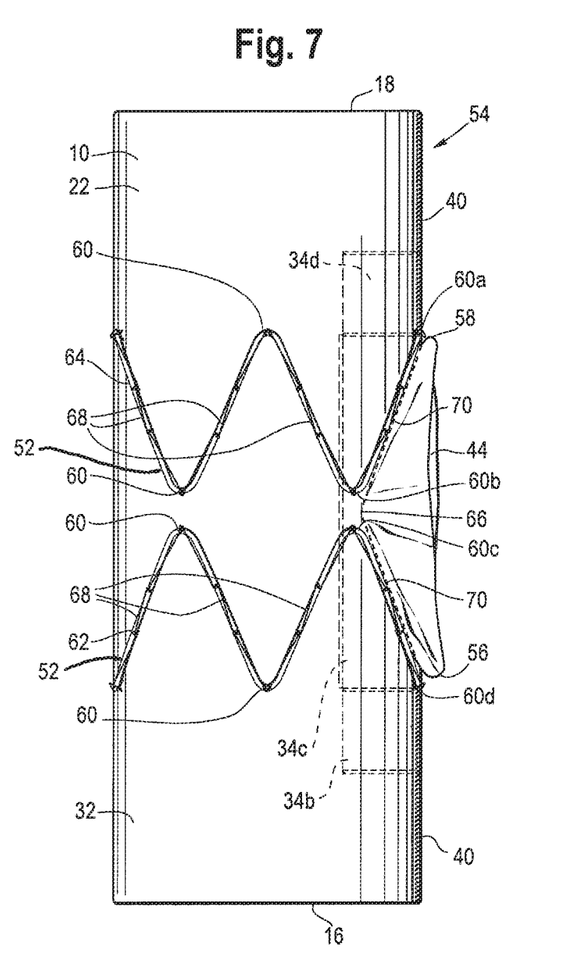
FIG. 7 shows an alternate side view of the tubular segment of graft material of FIG. 1 after being turned inside out and cut to expose free edges of an opening of the bidirectional branch.

FIG. 7 shows a side view of the endoluminal prosthesis 54 with the internal bidirectional branch 48. To increase the size of the opening 44 to allow access to the internal bidirectional branch 48 from several directions, the graft material surrounding the opening 44 and within the quadrilateral formed between the first and second rows 62, 64 of Z-stents surrounding the opening 44 are puckered to facilitate cutting the graft material adjacent to the Z-stents and within the quadrilateral. Specifically, for illustrative purposes, FIG. 7 shows a cutting line 66 that begins at the apex 60a of the second row 64 of Z-stents adjacent to the distal end 58 of the opening 44 and continues along a straight segment 68 of the second row 64 of Z-stents away from the opening 44 until the subsequent apex 60b of the second row 64 of Z-stents. The cutting line 66 then extends from the apex 60b of the second row 64 of Z-stents to the adjacent apex 60c of the first row 62 of Z-stents and continues along a straight segment 68 of the first row 62 of Z-stents toward the opening 44 until the apex 60d of the first row 62 of Z-stents adjacent to the proximal end 56 of the opening 44. A corresponding cutting line is located on the opposite side of the opening 44 (not shown).

Figure 8:
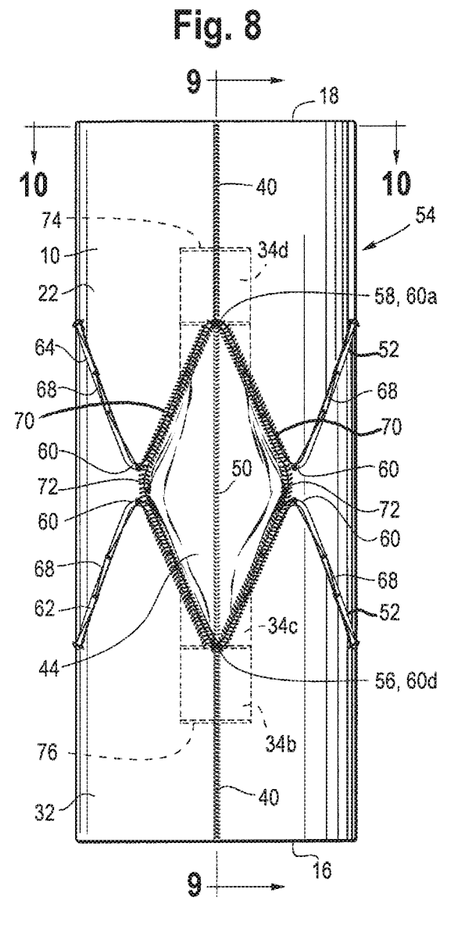
FIG. 8 shows an alternate side view of the tubular segment of graft material of FIG. 1 turned inside out and after attaching the free edges of the opening of the bidirectional branch to the graft material and/or plurality of stents.

The exterior of the graft material is cut along the cutting line 66 on both sides of the opening 44 such that free edges 70 of the graft material are formed. The opening 44 is increased to be the size of the quadrilateral between the first row 62 and the second row 64 of Z-stents by opening and/or pushing the graft material inward toward the interior of the main lumen 46 of the endoluminal prosthesis 54, and then the free edges 70 of the graft material are attached to the graft material and/or the stents 52 where the graft material was initially cut, as shown in FIG. 8. The free edges 70 may be connected to the graft material near the stents 52 via tacks to facilitate stitching or sewing of the free edges 70 back to the graft material near the stents 52 and/or to the stents 52. During stitching or sewing, the tacks may be removed. FIG. 8 shows a sewing line 72 where the free edges 70 are connected to the graft material near the stents 52 and/or to the stents 52. FIG. 8 also shows the increased size of the opening 44 that mirrors the size of the quadrilateral between the first and second rows 62, 64 of Z-stents between the apices 60 of the Z-stent located near the proximal and distal ends 56, 58 of the opening 44. In other examples, when different stent shapes are used, the opening 44 may be similarly puckered, cut and attached to the graft material and/or stents 52 to mirror the shape between two rows of stents 52 and to increase the size of the opening 44 of the internal bidirectional branch 48 to facilitate ease of cannulation and the ability to access the internal bidirectional branch 48 from the exterior of the endoluminal prosthesis 54 from several angles or directions.

Figure 9:
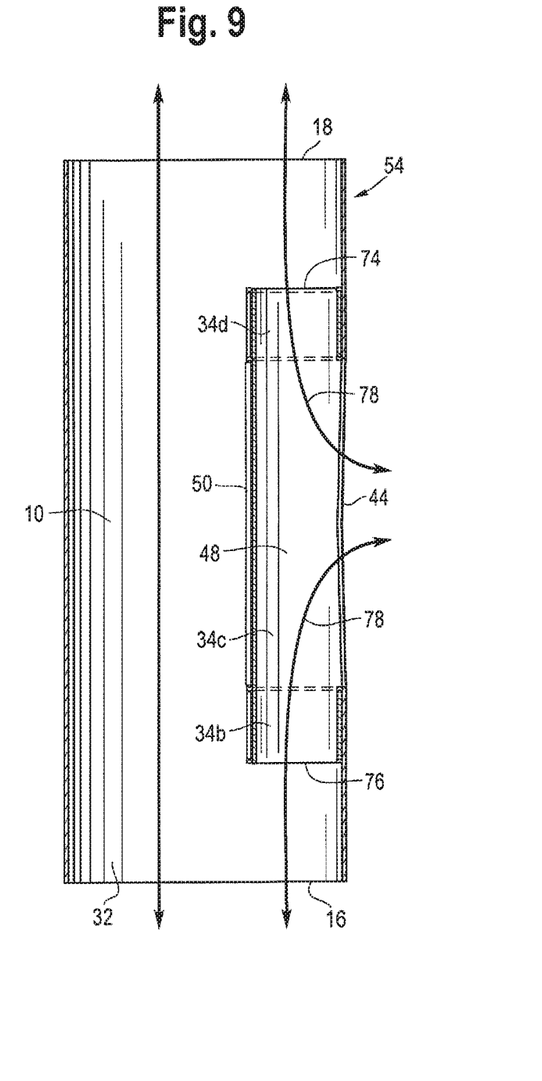
FIG. 9 shows a cross-sectional side view of the endoluminal prosthesis with the internal bidirectional branch of FIG. 8 taken along lines 9-9.
Figure 10:
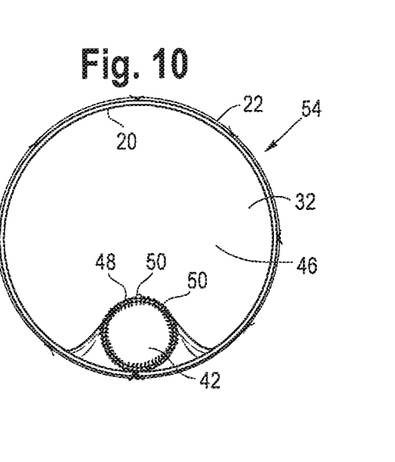
FIG. 10 shows an end view of the endoluminal prosthesis with the internal bidirectional branch of FIG. 8 taken along lines 10-10.

FIG. 9 shows a cross-sectional side view of the internal bidirectional branch 48 positioned internally within the main lumen 46 of the endoluminal prosthesis 54, and FIG. 10 shows an end view of the internal bidirectional branch 48 with the main lumen 46 of the endoluminal prosthesis 54. With the construction and positioning of the internal bidirectional branch 48, during cannulation, a cannula or tube may be inserted through the opening 44 of the internal bidirectional branch 48 and then exit the internal bidirectional branch 48 either through a distal end 74 of the internal bidirectional branch 48 toward the distal end 18 of the endoluminal prosthesis 54 or through a proximal end 76 of the internal bidirectional branch 48 toward the proximal end 16 of the endoluminal prosthesis 54. Alternatively, the cannula or tube may be inserted through the internal bidirectional branch 48 either through the distal end 74 and out of the opening 44 or through the proximal end 76 of the internal bidirectional branch 48 and out of the opening 44. The arrows 78 in FIG. 9 show the respective two directions that a cannula or tube may exit the internal bidirectional branch 48.

Figure 11:
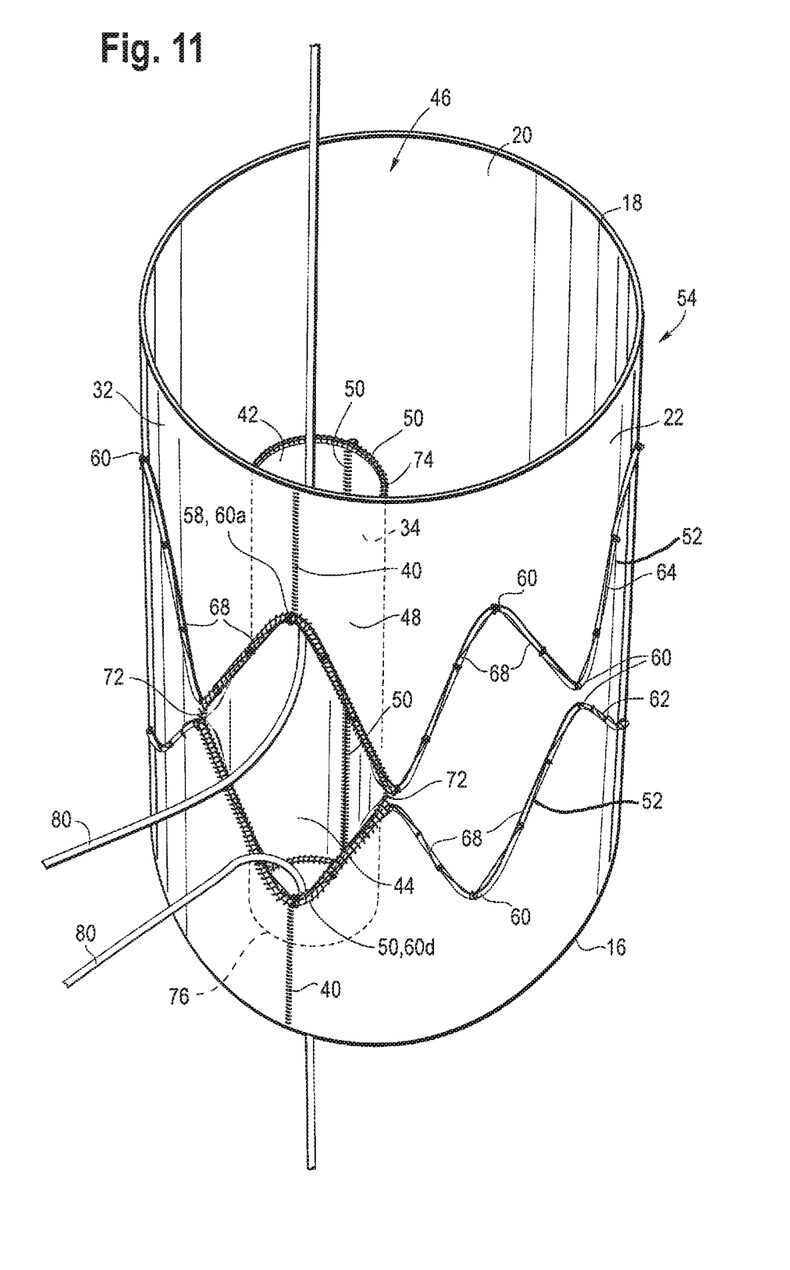
FIG. 11 shows a perspective view of cannulating the endoluminal prosthesis with the internal bidirectional branch in at least two directions.

FIG. 11 shows a perspective view of two cannulas or tubes 80 inserted through the opening 44 of the internal bidirectional branch 48 with one tube 80 extending out of the distal end 74 of the internal bidirectional branch 48 and the distal end 18 of the endoluminal prosthesis 54 and the second tube 80 extending out of the proximal end 76 of the internal bidirectional branch 48 and the proximal end 16 of the endoluminal prosthesis 54.

Advantageously, the present embodiments allow for the construction of an endoluminal prosthesis with an internal bidirectional branch from a single piece of graft material. The simplified construction decreases the number of materials, costs, and manufacturing time to make an endoluminal prosthesis with an internal bidirectional branch. The simplified construction also eliminates the need for making a separate branch for connection to the endoluminal prosthesis. The simplified construction also decreases interference of multiple tubes or cannulas within the lumen of the endoluminal prosthesis.

As another advantage, the present embodiments enable cannulation of a branch vessel from several directions. Specifically, the enlarged opening of the internal bidirectional branch allows access to one or more the branch vessels and decreases the complexity of the trying to cannulate through a small opening. Also, for patients with closely spaced branch vessels, the enlarged opening of the internal bidirectional branch also allows for multiple cannulas and/or tubes to be inserted through the opening. The enlarged opening of the internal bidirectional branch also allows cannulation is multiple directions when it may not be clear if the vessel is best cannulated from one direction.

As another advantage, the present embodiments enable cannulation through at least two directions within the internal bidirectional branch. Specifically, cannulation may occur through either the proximal or distal ends of the internal bidirectional branch. The multiple exits of the internal branch allows for the insertion of multiple cannulas or tubes with decreased interference within the internal bidirectional branch and the ability to access the branched vessel from different directions within the endoluminal prosthesis.

It will be appreciated by those skilled in the art that changes could be made to the embodiments described above without departing from the broad inventive concept therefore. It is understood, therefore, that this invention is not limited to the particular embodiments disclosed, but it is intended to cover modifications within the spirit and scope of the present invention as defined by the claims.

We claim:

1. A method of making a bidirectional branch within an endoluminal prosthesis, the method comprising:

laying a tubular segment of graft material flat, the tubular segment of graft material comprising a first lateral edge, a second lateral edge, a width extending from the first lateral edge to the second lateral edge, and a length extending from a proximal end to a distal end of the tubular segment;

partitioning the tubular segment into first and second sections along the length of the tubular segment, wherein the first section extends from the first lateral edge toward the second lateral edge and comprises a width less than the width of the tubular segment, and wherein the second section extends from the second lateral edge toward the first lateral edge and comprises a width less than the width of the first section such that a total width of the first and second sections is the same as the width of the tubular segment;

partitioning the second section of the tubular segment into at least three sub-sections, each of the at least three sub-sections having a proximal end, a distal end, and a length from the proximal end to the distal end, a first sub-section extending from the proximal end toward the distal end for a length from the proximal end of the second section to a distal end of the first sub-section, a second sub-section extending from the distal end of the first sub-section toward the distal end for a length from the distal end of the first sub-section to the distal end of the second sub-section, and a third sub-section extending from the distal end of the second sub-section to the distal end of the third sub-section for a length from the distal end of the second sub-section to the distal end of the third sub-section; wherein cumulative length of the three sub-sections is the same as the length of the tubular segment;

connecting the tubular segment along a lateral edge of the first sub-section from the proximal end to the second sub-section and along a lateral edge of the third sub-section from the distal end to the second sub-section, wherein the lateral edges of the first and third sub-sections are opposite the second lateral edge of the tubular segment; and turning the tubular segment inside out such that the first, second and third sub-sections of the second section form the bidirectional branch, the bidirectional branch is positioned within a lumen of the endoluminal prosthesis and an opening of the second sub-section is exposed to an exterior of the tubular segment.

2. The method of claim 1 further comprising connecting wire to the graft material around first and second ends of the first sub-section and first and second ends of the third sub-section to support the patency of the first and third sub-sections.

3. The method of claim 1 further comprising connecting wire along the second lateral edges of the first, second and third sub-sections.

4. The method of claim 1, wherein connecting the tubular segment along the lateral edges of the first and third sub-sections comprises sewing or stitching.

5. The method of claim 1 further comprising connecting a plurality of stents to an exterior surface of the endoluminal prosthesis after turning the tubular segment inside out.

6. The method of claim 5, wherein at least two of the plurality of stents comprise a Z-stent, and the method further comprising positioning the at least two Z-stents around the opening of the second sub-section to form a quadrilateral.

7. The method of claim 6 further comprising cutting the tubular segment along the quadrilateral of the at least two Z-stents to expose free edges of the opening.

8. The method of claim 7 further comprising connecting the free edges of the opening to the graft material of the tubular segment proximate to the at least two Z-stents.

9. A method of making an internal bidirectional branch for an endoluminal prosthesis from a tubular segment of graft material, the method comprising:

partitioning the tubular segment of graft material into first and second tubular sections, the tubular segment having a lumen, a diameter, and a length extending from a proximal end to a distal end of the tubular segment, and each tubular section having the same length as the tubular segment of graft material;

wherein the first tubular section comprises a diameter less than the diameter of the tubular segment of graft material and the second tubular section comprises a diameter less than the diameter of the first tubular section such that a total diameter of the first and second tubular sections is the same as the diameter of the tubular segment of graft material;

partitioning the second tubular section into five sub-sections along the length of the tubular segment of graft material; wherein a cumulative length of the five sub-sections is the same as the length of the tubular segment of graft material;

wherein a first sub-section extends from the proximal end of the second tubular section toward the distal end of the second tubular section for a length from the proximal end of the second tubular section to a distal end of the first sub-section, a second sub-section extends from the distal end of the first sub-section toward the distal end for a length from the distal end of the first sub-section to a distal end of the second subsection, a third sub-section extends from the distal end of the second sub-section toward the distal end for a length from the distal end of the second sub-section to a distal end of the third sub-section, a fourth sub-section extends from the distal end of the third sub-section toward the distal end for a length from the distal end of the third sub-section to a distal end of the fourth sub-section, and a fifth sub-section extends from the distal end of the fourth sub-section to the distal end of the second tubular section and comprises a length from the distal end of the fourth sub-section to the distal end of the second tubular section;

connecting the tubular segment of graft material along the first, second, fourth, and fifth sub-sections of the second tubular section to separate the first tubular section and the second tubular section;

removing the first and fifth sub-sections of the second tubular section from the tubular segment while maintaining connected edges of the first and fifth subsections such that the second, third and fourth subsections form the bidirectional branch; and turning the tubular segment inside out such that the bidirectional branch is positioned within a main lumen of the endoluminal prosthesis and an opening of the third sub-section is exposed to an exterior of the third sub-section.

10. The method of claim 9 further comprising connecting wire to the graft material around first and second ends of the second sub-section and first and second ends of the fourth sub-section to support the patency of the second and fourth sub-sections.

11. The method of claim 9, wherein connecting the tubular segment of graft material along the first, second, fourth and fifth sub-sections of the second tubular section comprises sewing or stitching.

12. The method of claim 9 further comprising connecting a plurality of stents to an exterior surface of the endoluminal prosthesis after turning the tubular segment inside out.

13. The method of claim 12, wherein at least two of the plurality of stents comprise a Z-stent, and the method further comprising positioning the at least two Z-stents around the opening of the third sub-section to form a quadrilateral.

14. The method of claim 13 further comprising puckering the opening of the third sub-section, and cutting the tubular segment along the quadrilateral of the at least two Z-stents to form free edges of the opening.

15. The method of claim 14 further comprising connecting the free edges of the opening to the graft material of the tubular segment proximate to the at least two Z-stents.

16. The method of claim 9, wherein each sub-section of the second tubular section has a diameter that is the same as the diameter of the second tubular section.

17. The method of claim 16, wherein at least two of the plurality of stents comprise a Z-stent, and the method further comprising positioning the at least two Z-stents around the opening of the second sub-section to form a quadrilateral.

18. The method of claim 17 further comprising cutting the graft material of the tubular segment along the quadrilateral of the at least two Z-stents to expose free edges of the opening.

19. The method of claim 18 further comprising connecting the free edges of the opening to the graft material of the tubular segment proximate to the at least two Z-stents.

20. A method of making an internal bidirectional branch for an endoluminal prosthesis, the method comprising:

laying a tubular segment of graft material flat, the tubular segment of graft material comprising a first lateral edge, a second lateral edge, a width extending from the first lateral edge to the second lateral edge, and a length extending from a proximal end to a distal end of the tubular segment;

partitioning the tubular segment into first and second sections along the length of the tubular segment, wherein the first section extends from the first lateral edge toward the second lateral edge and comprises a width less than the width of the tubular segment, and wherein the second section extends from the second lateral edge toward the first lateral edge and comprises a width less than the width of the first section such that a total width of the first and second sections is the same as the width of the tubular segment;

partitioning the second section of the tubular segment into at least three sub-sections, each sub-section having the width of the second section, a first sub-section extending from the proximal end of the tubular segment toward the distal end for a length from the proximal end of the tubular segment to a distal end of the first sub-section, a second sub-section extending from the distal end of the first sub-section toward the distal end for a length from the distal end of the first sub-section to a distal end of the second sub-section, and a third sub-section extending from the distal end of the second sub-section to the distal end for a length from the distal end of the second sub-section to the distal end of the tubular segment; wherein a cumulative length of the three sections is the same as the length of the tubular segment;

connecting the tubular segment along a lateral edge of the first sub-section from the proximal end to the second sub-section and along a lateral edge of the third sub-section from the distal end to the second sub-section, wherein the lateral edges of the first and third sub-sections are opposite the second lateral edge of the tubular segment;

turning the tubular segment inside out such that the first, second and third sub-sections of the second section form the bidirectional branch, the bidirectional branch is positioned within a lumen of the endoluminal prosthesis, and an opening of the second sub-section is exposed to an exterior of the tubular segment; and connecting a plurality of stents to an exterior surface of the endoluminal prosthesis.

* * * * *